(12) United States Patent
Stark

(10) Patent No.: US 8,933,028 B2
(45) Date of Patent: *Jan. 13, 2015

(54) USE OF SELECTIVE ESTROGEN RECEPTOR MODULATOR FOR JOINT FUSION AND OTHER REPAIR OR HEALING OF CONNECTIVE TISSUE

(71) Applicant: John G. Stark, Deephaven, MN (US)

(72) Inventor: John G. Stark, Deephaven, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,344

(22) Filed: Jul. 3, 2013

(65) Prior Publication Data

US 2013/0295202 A1    Nov. 7, 2013

Related U.S. Application Data

(63) Continuation of application No. 12/771,752, filed on Apr. 30, 2010, now Pat. No. 8,501,690.

(51) Int. Cl.
| | |
|---|---|
| *A61K 38/00* | (2006.01) |
| *A61K 31/4535* | (2006.01) |
| *A61K 31/138* | (2006.01) |
| *A61K 31/40* | (2006.01) |
| *A61K 31/4025* | (2006.01) |
| *A61K 31/55* | (2006.01) |
| *A61K 31/56* | (2006.01) |
| *A61K 33/06* | (2006.01) |
| *A61K 38/18* | (2006.01) |
| *A61K 45/06* | (2006.01) |
| *A61K 31/59* | (2006.01) |
| *A61K 38/19* | (2006.01) |

(52) U.S. Cl.
CPC ........... *A61K 31/4535* (2013.01); *A61K 31/138* (2013.01); *A61K 31/40* (2013.01); *A61K 31/4025* (2013.01); *A61K 31/55* (2013.01); *A61K 31/56* (2013.01); *A61K 33/06* (2013.01); *A61K 38/1875* (2013.01); *A61K 45/06* (2013.01); *A61K 38/1841* (2013.01); *A61K 31/59* (2013.01); *A61K 38/19* (2013.01)
USPC .......................................................... 514/9.7

(58) Field of Classification Search
None
See application file for complete search history.

(56) References Cited

U.S. PATENT DOCUMENTS

| | | | |
|---|---|---|---|
| 4,133,814 A | 1/1979 | Jones et al. | |
| 4,380,635 A | 4/1983 | Peters | |
| 4,418,068 A | 11/1983 | Jones | |
| 5,013,649 A | 5/1991 | Wang et al. | |
| 5,118,667 A * | 6/1992 | Adams et al. | 514/8.5 |
| 5,119,667 A | 6/1992 | Hollis et al. | |
| 6,124,314 A * | 9/2000 | Cameron et al. | 514/307 |
| 6,894,064 B2 | 5/2005 | Arbuthnot et al. | |
| RE39,050 E | 3/2006 | Draper et al. | |
| 7,261,875 B2 | 8/2007 | Li et al. | |
| 7,332,525 B2 | 2/2008 | Castle | |
| 7,425,565 B2 | 9/2008 | Agus | |
| 7,479,279 B2 | 1/2009 | Paulista et al. | |
| 7,504,374 B2 | 3/2009 | Marx et al. | |
| 7,563,455 B2 | 7/2009 | McKay | |
| 7,648,509 B2 * | 1/2010 | Stark | 606/90 |
| 8,501,690 B2 * | 8/2013 | Stark | 514/9.7 |
| 2002/0019351 A1 | 2/2002 | Ke et al. | |
| 2003/0162807 A1 * | 8/2003 | Day et al. | 514/307 |
| 2005/0037089 A1 | 2/2005 | Jobbins | |
| 2005/0147562 A1 | 7/2005 | Hunter et al. | |
| 2005/0271637 A1 | 12/2005 | Bodine et al. | |
| 2007/0135407 A1 | 6/2007 | Steiner | |
| 2008/0175905 A1 | 7/2008 | Liu et al. | |
| 2009/0024174 A1 | 1/2009 | Stark | |
| 2009/0202638 A2 | 8/2009 | Hidaka et al. | |
| 2010/0106200 A1 | 4/2010 | Stark | |

FOREIGN PATENT DOCUMENTS

WO          03/020329 A1        3/2003

OTHER PUBLICATIONS

Cosman et al., "Clinical and Mechanistic Insights Into Novel Agents in Development for Osteoporosis," Current Medical Evidence, Apr. 2009, vol. 2, Issue 5.
Deckers et al, "Bone Morphogenic Proteins Stimulate Angiogenesis through Osteoblast-Derived Vascular Endothelial Growth Factor A," Endocrinology 2002; 143(4):1545-1553.
Gendimenico et al. "Tropical estrogens: their effects on connective tissue synthesis in hairless mouse skin." Arch Dermatol Res. 2002; 294(5):231-236 (Abstract only).
Hettrich et al, "The Effect of Recombinant Human Parathyroid Hormone on the Healing of Tendon to Bone in a Rat Model," Poster No. 1105 from the 56th Annual Meeting of the Orthopaedic Research Society, 2010.
Irie et al., "Effect of Selective Estrogen Receptor Modulator/Raloxifene Analogue on Proliferation and Collagen Metabolism of Tendon Fibroblast," Poster No. 1117 from the 56th Annual Meeting of the Orthopaedic Research Society, 2010.

(Continued)

*Primary Examiner* — Anand Desai
*Assistant Examiner* — Melissa Mercier
(74) *Attorney, Agent, or Firm* — Dardi & Herbert, PLLC; Peter S. Dardi

(57) ABSTRACT

Methods for facilitating joint immobilization or fusion using selective estrogen receptor modulator (SERM) such as raloxifene are disclosed. The SERM may be administered systemically or locally. In conjunction with SERM, other therapeutic agents such as calcium, vitamin D, bone morphogenetic protein may be administered simultaneously. The method can similarly be applied to facilitate bone repair, bone healing, and connective tissue healing processes in a patient.

25 Claims, 7 Drawing Sheets

(56) References Cited

OTHER PUBLICATIONS

Kalfas et al., "Principles of Bone Healing," Neurosurg Focus, 2001; 10(4).

Kato et al., "Raloxifene inhibits TNF-α induced apoptosis via JNK-BAD signaling pathway in osteoblastic cells," Poster No. 525 from the 56th Annual Meeting of the Orthopaedic Research Society, 2010.

Kawaguchi et al., "Acceleration of Fracture Healing in Nonhuman Primates by Fibroblast Growth Factor-2," J Clin Endrocrinol Metab 2001; 86(2):875-880.

Lufkin et al., "Treatment of Established Postmenopausal Osteoporosis with Raloxifene: A Randomized Trail," J Bone Miner Res 1998; 13(11):1747-1754.

Prestwood et al., "A Comparison of the Effects of Raloxifene and Estrogen on Bone in Postmenopausal Women," Journal of Clinincal Endocrinology and Metabolism 2000; 85(6):2197-2202.

Sambrook et al., "Alendronate produces greater effects than raloxifene on bone density and bone turnover in postmenopausal women with low bone density: results of EFFECT (Efficacy of FOSAMAX® versus EVISTA® Comparison Trial) International," Journal of Internal Medicine 2004; 255:503-511.

Snyder et al., "Raloxifene hydrochloride," Am J Health Syst Pharm. 2000; 57(18):1669-1678 (Abstract only).

Tanaka et al., "1,25-Dihydroxy-vitamin D3 Regulates Myotube Formation through Vitamin D REceptor Mediated Signal," Poster No. 1595 from the 56th Annual Meeting of the Orthopaedic Research Society, 2010.

Taranta et al., "The selective estrogen receptor modulator raloxifene regulates osteoclast and osteoblast activity in vitro," Bone, Feb. 2002: 30(2):368-76 (Abstract only).

Product Information for INFUSE® Bone Graft—rhBMP2, "Instructions for Preparation and Surgical Application for Open Tibial Fracture," produced by Medtronic Sofamor Danek USA, Inc., 2005.

International Search Report and Written Opinion for application No. PCT/US 11/32839 dated Aug. 19, 2011 (10 pages).

* cited by examiner

USE OF SELECTIVE ESTROGEN RECEPTOR MODULATOR FOR JOINT FUSION AND OTHER REPAIR OR HEALING OF CONNECTIVE TISSUE

CROSS REFERENCE TO RELATED APPLICATIONS

This application is a continuation of copending U.S. patent application Ser. No. 12/771,752 to Stark filed on Apr. 30, 2010, entitled "Use of Selective Estrogen Receptor Modulator for Joint Fusion and Other Repair or Healing of Connective Tissue," incorporated herein by reference.

FIELD OF THE INVENTION

The inventions in general are related to the method of using selective estrogen receptor modulators (SERMs) to facilitate joint fusion. The inventions are further related to methods of using SERMs to facilitate bone repair, bone healing, or connective tissue healing processes in general.

BACKGROUND

Bone is a dynamic biological tissue composed of metabolically active cells that are integrated into a rigid framework. The healing potential of bone, whether in a fracture or fusion model, is influenced by a variety of biochemical, biomechanical, cellular, hormonal, and pathological mechanisms. A continuously occurring state of bone deposition, resorption, and remodeling facilitates the healing process. The success of many spine operations depends on the restoration of long-term spinal stability. Whereas spinal instrumentation devices may provide temporary support, a solid osseous union is desired to provide long term stability. The failure of fusion to occur may result in the fatigue and failure of supporting instrumentation and persistence or worsening of symptoms.

Bone metabolism is regulated by a host of hormonal and local factors. Three of the calcitropic hormones that affect bone metabolism are parathyroid hormone, vitamin D, and calcitonin. Bone metabolism is also affected by a series of proteins, or growth factors, released from platelets, macrophages, and fibroblasts. These proteins cause healing bone to vascularize, solidify, incorporate, and function mechanically. They can induce mesenchymal-derived cells, such as monocytes and fibroblasts, to migrate, proliferate, and differentiate into bone cells. The proteins that enhance bone healing include the BMPs, insulin-like growth factors, transforming growth factors, platelet derived growth factor, and fibroblast growth factor, among others.

SUMMARY OF THE INVENTION

In one aspect, the invention relates to a method for facilitating joint immobilization or fusion. The method comprises the step of administering a composition comprising an effective amount of a selective estrogen receptor modulator (SERM) to a patient who has received an immobilization element interfacing with a joint, to result in joint immobilization or fusion. In some embodiments, the SERM is administered directly to the joint or surrounding tissue to access the immobilization element to facilitate joint immobilization or fusion. In other embodiments, the SERM is administered systemically. Auxiliary agents such as calcium, vitamin D, or a combination thereof may be administered systemically in addition to the SERM to improve bone healing. Therapeutic agents such as nutritional factors, endocrine factors, growth factors, synthetic or natural anabolic steroids, or a combination thereof may be administered in addition to the SERM to improve bone healing. SERM in general includes afimoxifene (4-hydroxytamoxifen), arzoxifene, bazedoxifene, clomifene, femarelle, lasofoxifene, ormeloxifene, tamoxifen, toremifene, analogs or derivatives thereof, or a combination thereof. In one embodiment, the SERM used is raloxifene, analogs or derivatives thereof, or a combination thereof. In some embodiments, a bone morphogenetic protein (BMP), or cellular cytokine may be administered in addition to the SERM to the joint to access the immobilization element to facilitate joint immobilization or fusion. Suitable BMP includes BMP-2, BMP-7, or a combination thereof. Suitable cytokine includes one or members of the transforming growth factor beta (TGF-β) super family. In one embodiment, the fusion or immobilization involves fusion of adjacent vertebrae or fusion of the sacroiliac joint. In another embodiment, the fusion or immobilization is fracture union between traumatically induced fractures, stress fractures, or un-united fractures. In some embodiments, the composition may be administered prior to the joint fusion or immobilization procedure.

In a second aspect, the invention relates to a method for facilitating a bone repair process in a patient. The method comprises administering an effective amount of a composition comprising a selective estrogen receptor modulator (SERM) to the patient to stimulate the bone repair process wherein the patient has been provided a bone morphogenetic protein (BMP) to a location selected for bone repair. In some embodiments, the composition is also administered to the location selected for bone repair. A suitable patient for the method can be a post-menopausal woman. The bone repair method can be applied to fracture union between traumatically induced fractures, stress fractures, or un-united fractures. In some embodiments, the composition may be administered prior to the bone repair procedure.

In a third aspect, the invention relates to a method for the improvement of bone healing. The method comprises administering an effective amount of composition comprising a selective estrogen receptor modulator (SERM) to a patient to improve the bone healing process. In some embodiments, the patient also receives bone graft, bone substitute or other osteoconductive material. In some embodiments, the bone healing is in non-surgically treated patients.

In a fourth aspect, the invention relates to a method for facilitating healing of connective tissue. The method comprises administering a composition comprising an effective amount of a selective estrogen receptor modulator (SERM) to a patient to result in improvement in healing of the connective tissue. The patient may have connective tissue injury including laceration, contusion, ischemia, anoxia, or avulsion of the connective tissue. Additionally, the patient may have congenital, endocrine, or nutritional imbalance related to connective tissue. In some embodiments, the patient receives soft tissue autograft or allograft. In other embodiments, the patient receives prosthesis, scaffold, or attaching implant to facilitate connective tissue continuity. In one embodiment, the connective tissue comprises the intervertebral disc. The connective tissue may comprise tendon, ligament, bone, dysvascular connective tissue, or their interrelationships and connections. In one embodiment, the composition is controllably released from a suture.

DETAILED DESCRIPTION OF PREFERRED EMBODIMENTS

Figure 1:
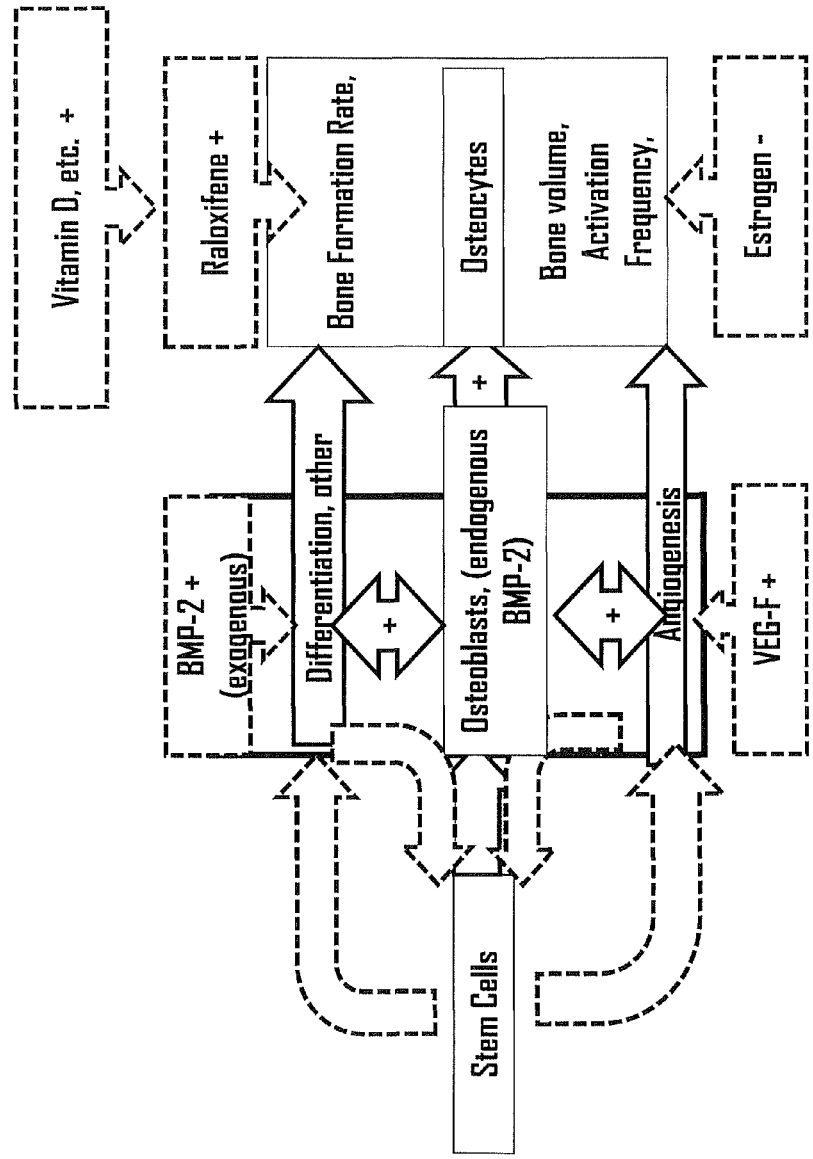
FIG. 1 is a schematic drawing of a simplified scheme of bone healing with or without exogenous stimulants.

It has been discovered that the administration of a SERM can significantly improve bone turnover and metabolic activity, and by analogy bone healing can be similarly improved through the administration of a SERM. In many postmenopausal women after bone fusion or immobilization surgery, complications arise when the treated bone does not fuse well. Insufficient hormonal levels such as falloff of estrogen, parathyroid hormone, growth hormone, thyroid hormone, and insulin have been attributed to the generalized deficiency of the bone healing response in post menopausal women. While the local administration of bone morphogenetic proteins has had some success in facilitating bone fusion processes, the combination of BMP with a SERM has achieved unexpected synergies. While the effectiveness of SERMs would be expected to be particularly pronounced in post menopausal women, the usefulness of SERMs for bone fusion and general bone healing can be expected to extend to all individuals with or without the combination with BMP. Based on the physiological effects of SERMs generally on connective tissue, SERMs may be desirable agents to be administered generally to promote the healing of connective tissues, such as ligaments, tendons, intevertebral discs, dysvascular tissues, cartilage and other connective tissues in addition to bone, whether or not associated with bone. Connective tissue healing, used herein, refers to the general recovery of soft tissues, such as ligaments or tendons as well as bone and cartilage, and includes healing situations that may involve more than one tissue type, such as tendon to bone, or ligament to bone. Such processes may comprise initiation or acceleration of cellular differentiation and division, secretion of intracellular matrix, or other cellular processes such as apoptosis, resorption or vascular ingrowth.

For bone healing procedures, forces that improve the healing process can reduce the rate of failure of these procedures, the need of pain medication, time off from work, and/or the general debility which complicates the recovery. Improving the result of the healing process and/or accelerating the healing, can reduce costs associated with continued care of the patient and reduce costs associated with leaves from work as well as improve quality of life for the patient. The phrase "bone healing" in general is used herein to refer to the general recovery of joint fusion or immobilization, bone grafting, bone healing, bone repairing, or a combination of these processes. In some embodiments, bone healing refers to bone healing with no surgical intervention. The term "union" used herein refers to bone cell formation, secretion, and organization of functional bone that are achieved in the bone healing process.

In bone loss related disease such as osteoporosis, one of the important diagnostic factors is bone mineral density (BMD), a medical term referring to the amount of bone matter per cubic centimeter of bone. BMD is tightly regulated by a balance between osteoblasts, mononucleate cells that are responsible for bone formation and osteoclasts, a type of bone cell that removes bone tissue by removing its mineralized matrix and breaking up the organic bone. Stimulation of osteoblasts and inhibition of osteoclasts therefore can help to accelerate bone turnover and/or increase BMD and subsequently prevent or even reverse bone loss. SERMs such as raloxifene are believed to reduce osteoclast number and osteoclast-mediated resorption and also induce osteoblast proliferation as disclosed by Cosman et al., in Current Medical Evidence, Vol. 2, Issue 5, entitled "Clinical and Mechanistic Insights into Novel Agents in Development for Osteoporosis", incorporated herein by reference. Cosman in fact classified raloxifene under the category of anti-resorptive or anti-catabolic agents as oppose to anabolic agents such as parathyroid hormone, the other class of osteoporosis drugs.

In bone healing/fusion related processes however, in addition to bone formation, reorganization and revascularization of the bone and connective tissues are believed to be important factors. A certain degree of bone resorption therefore is believed to be important to allow the reorganization and revascularization of the bone and connective tissues to occur. As discussed herein, in addition to stimulating bone formation, SERMs appear to facilitate the bone reorganization and revascularization processes, thus the healing/fusion of the bone. Thus, it is demonstrated herein that SERMs can also contribute to bone healing, facilitating bone fusion and other connective tissue healing and tissue maturation processes, whether or not the other connective tissue is associated with bone.

In addition to repairs of broken bones and other bone repair processes, bone fusion can be used to alleviate pain for certain joints. For example, fusion of vertebrae can be useful for reducing back pain. Also, recently fusion of the sacroiliac joint has been found to be effective at reducing lower back pain that has been non-responsive to other forms of treatment. See, U.S. Pat. No. 7,648,509 to Stark, entitled "Sacroiliac Joint Immobilization," incorporated herein by reference (the '509 patent). The sacroiliac joint is not generally amenable to joint replacement.

As described in the '509 patent exogenous BMP has been used in the performance of sacroiliac joint fusion procedures. Also, recombinant exogenous BMP has US-FDA approval for use in certain spinal fusion procedures. However, in some individuals, the fusion process with or without BMP has been found to be deficient. The deficiencies of the fusion process for sacroiliac joint fusions were found to be particularly prevalent in postmenopausal women. It was discovered that the administration of SERMs resulted in significant improvement in the joint fusion in postmenopausal women and based on the superior fusion results in postmenopausal women relative to other individuals, it follows that SERMs can be useful in other individuals or patient groups to improve bone fusion and bone healing results.

Parathyroid hormone increases the flow of calcium into the calcium pool and maintains the body's extracellular calcium levels at a relatively constant level. This hormone can induce cytoskeletal changes in osteoblasts. Vitamin D stimulates intestinal and renal calcium-binding proteins and facilitates active calcium transport. Calcitonin is secreted by the parafollicular cells of the thyroid gland in response to an acutely rising plasma calcium level. Calcitonin serves to inhibit calcium-dependent cellular metabolic activity.

Bone morphogenetic proteins induce mesenchymal cells to differentiate into bone cells. Although typically present in only minute quantities in the body, several BMPs have been synthesized using recombinant DNA technology and have undergone clinical trials to assess their potential to facilitate bone fusion in humans. Other proteins influence bone healing in different ways. Transforming growth factor and related chemicals regulate angiogenesis, bone formation, extracellular matrix synthesis, and controls cell-mediated activities. Osteonectin, fibronectin, osteonectin, and osteocalcin promote cell attachment, facilitate cell migration, and activate cells.

The hormonal and local factors as well as growth factors can be supplemented in patients. Additionally, small molecule medication can be used to treat bone related disorders. For instance, selective estrogen receptor modulators (SERMs) are used to treat osteoporosis most notably in post menopausal women patients. SERMs are drugs that activate or inhibit the estrogen receptors on different tissues. SERMs can act like estrogen in the desirable ways such as stabilizing bone mass, improving lipid profile, reducing hot flashes, but may not act like estrogen in undesirable ways such as causing breast cancer or stimulating the endometrium. If appropriately chosen, the SERM can be particularly desirable to exploit for other healing possibilities.

The bone healing process in general is demonstrated to be facilitated by the use of selective estrogen receptor modulator (SERM) such as raloxifene. In particular, the combination of a SERM with exogenous BMP such as BMP-2 has yielded excellent fusion of sacroiliac joints for postmenopausal women. Nutritional supplements such as vitamin D and calcium, endocrine factors, growth factors, and synthetic or natural anabolic steroids alone or combined can be used in conjunction with SERM and/or BMP-2 to facilitate the healing process.

In some embodiments, a SERM, such as raloxifene, can be administered locally or systemically. For example, for systemic administration, the SERM can be ingested at appropriate intervals orally, such as in pill form. In additional or alternative embodiments, a composition containing an effective amount of a SERM can be administered directly to or around the site where bone healing is expected to occur. Local delivery of a SERM may be particularly desirable for some patients in which systemic delivery may be undesirable. In embodiments where an immobilization element is implanted to fuse bone structures, a SERM containing composition can be pre-applied to the immobilization element or the SERM can be independently delivered at the site. The term "immobilization element" used herein refers to bone graft, wedge, nail, bone screw, or any mechanical element that can be placed into or near a joint to facilitate bone stabilization or fusion. Similarly, bone healing elements can comprise joint prostheses, internal fixators, pins, clamps or other mechanical elements that can be used to facilitate bone healing or stabilization. In some embodiments, a SERM containing composition can be pre-applied to a prosthesis, such as a joint replacement orthosis, a scaffold or attaching implant, such as associated with an orthopedic repair, a soft tissue autograft, which involves re-location of a portion of a patient's connective tissue, a soft tissue allograft, which involves transplant tissue from a compatible donor or combinations thereof or the like. For joint fusions or general bone healing, a bone graft, bone substitute or other osteoconductive material can be used. An osteoconductive material provides a scaffolding of bone like material for bone in-growth. Bone graft or bone substitute materials include, for example, bone powder, bone segments, hydroxyapatite, tricalcium phosphate, other synthetic bone-like materials or the like or combinations thereof.

For sustained delivery, a SERM can be embedded in a controlled release vehicle such as a hydrogel. In some embodiments, a SERM can be administered in the form of an implant and a reservoir. Alternatively, a SERM can be administered systemically, topically, intravenously, intramuscularly, orally, rectally, with a patch, or locally. Generally, a SERM can be administered prior to, during, and/or after a bone treatment procedure, sometime for an extended period of time such as 3 months or more. Long term systemic oral delivery of raloxifene at a dosage of 60 mg/day for example has been routinely administered to postmenopausal women for treatment of osteoporosis. Side effects include, for example, hot flashes, leg cramps and blood clots are observed in some patients. Raloxifene has also been administered orally to male patients at 60 mg/day to treat prostate cancer in U.S. Pat. No. 7,425,565 to Agus et al. entitled "Use of Benzothiophenes to Treat and Prevent Prostate Cancer", incorporated herein by reference showing similar side effects as in female patients, although co-administration of estrogen inhibitor is recommended. Raloxifene thus appears to be safe in both male and female patients.

The treatment options described herein can be used to improve fusion of vertebrae, sacroiliac joint fusion, fracture union between traumatically induced fractures, stress fractures, or un-united fractures, bone repair, and bone healing in general. With appropriate adaptation of administration route and timing, the treatment can be applied to both female and male patients. The treatment may be particularly useful for post menopausal female patients. In more generalized applications, the composition and methods described herein can be use to facilitate the healing of connective tissue in general. Patients with connective tissue injuries such as laceration, contusion, ischemia, anoxia, or avulsion may be treated with SERM containing compositions to facilitate the healing processes in general.

Selective Estrogen Receptor Modulator (SERM) in Connective Tissue Healing

As described herein, it has been discovered that SERMs are effective to facilitate healing of connective tissue, in particular bone. The healing can be associated with bone fusion. Selective Estrogen Receptor Modulators (SERMs) are a class of compounds that selectively act on estrogen receptors. A characteristic that distinguishes these substances from pure receptor agonists and antagonists is that their action is different in various tissues, thereby granting the possibility to selectively inhibit or stimulate estrogen-like action in various tissues. Phytoserms for example are considered SERMs from a botanical source. Other members of the SERM family include, for example, afimoxifene (4-hydroxytamoxifen), arzoxifene, idoxifene, bazedoxifene, clomifene, femarelle, lasofoxifene, ormeloxifene, tamoxifen, raloxifene, toremifene, combinations thereof and salts thereof. SERMs and medicinal formulations of SERMs are discussed generally in published U.S. patent application 2008/0175905A to Liu et al., entitled "Estrogen/SERM and Estrogen/Progestin Bi-Layer Tablets," and in U.S. Pat. No. 6,894,064 to Arbuthnot et al., entitled "Benzothiophene, Formulations Containing Same, and Methods", both incorporated herein by reference. In general, SERMs as used herein refer to known or future developed or discovered SERMs, as recognized generally in the art. Additionally, analogs or derivatives of SERMs can be similarly used. For example analogs or derivatives of raloxifene disclosed in U.S. Pat. No. 4,133,814 to Jones et al., entitled "2-Phenyl-3-aroylbenzothiophenes Useful as Anti-fertility Agents," U.S. Pat. No. 4,380,635 to Peters entitled "Synthesis of Acylated Benzothiophenes," and U.S. Pat. No. 4,418,068 to Jones entitled "Anti-estrogenic and Anti-androgenic Benzothiophenes," all incorporated herein by reference, can be selectively used based on activity and choice of method of delivery. Analogs refer to chemically similar compositions that can be recognized by a person of ordinary skill in the art to have an expected similar efficacy based on similar chemical structure, and derivatives refer to chemical derivatives that can be expected by a person of ordinary skill in the art to have similar activity based on the particular derivation of the original composition.

Historically, SERMs were referred to as anti-estrogens, but this term has fallen into disfavor due to inaccuracy of the more complex interactions now associated with SERMs. Depending on pattern of action, SERMs can be used in treatment of diseases in various tissues. For example, clomifene is used in anovulation, femarelle is used for managing menopause symptoms and maintaining bone health, ormeloxifene is used for contraception, raloxifene is used for the treatment and prevention of osteoporosis in postmenopausal women, and tamoxifen and toremifene are used for treatment related to breast cancer. Some SERMs may be suitable replacements for hormone replacement therapy (HRT) in some women. Some of the above agents still have significant side-effects which contraindicate widespread long term use.

In general, SERMs span a spectrum of activity ranging from full agonists (agonistic in all tissues) such as the natural endogenous hormone estrogen, mixed agonists/antagonists (agonistic in some tissues while antagonistic in others) such as tamoxifen, and pure antagonists (antagonistic in all tissues) such as fulvestrant (ICI-182780). The mechanism of mixed agonist/antagonist activities may differ depending on the chemical structure of the SERM. For example, the SERM tamoxifen acts as an antagonist in breast and conversely an agonist in uterus. The concentration of steroid receptor co-activator 1 (SRC-1; NCOA1) is higher in uterus than in breast, therefore SERMs such as tamoxifen are more agonistic in uterus than in breast. In contrast, raloxifene behaves as an antagonist in both tissues. It appears that raloxifene more strongly recruits co-repressor proteins and consequently is still an antagonist in the uterus despite the higher concentration of co-activators relative to co-repressors.

SERMs have effects on various tissues. Bone turnover and postmenopausal osteoporosis respond favorably to most SERMs. In breast, all SERMs decrease breast cancer risk, and tamoxifen is mainly used for its ability to inhibit growth in estrogen receptor-positive breast cancer. Cholesterol and triglycerides levels respond in general favorably to SERMs. The risk of deep venous thrombosis however may be elevated in at least some SERMs. Hot flashes are increased by some SERMs. Clomifene is known to act on pituitary gland by blocking estrogen action leading to an increase of follicle-stimulating hormone. In uterus, although tamoxifen may increase endometrial carcinoma risk, raloxifene and femarelle do not seem to have this side effect.

Raloxifene (6-hydroxy-2-(4-hydroxyphenye-benzothiophen-3-yl)]-[4-(2-(1-piperidyl) ethoxy)phenyl]-methanone) is an alternative to traditional hormone replacement therapy for the prevention and treatment of osteoporosis in selected postmenopausal women. The recommended dosage is 60 mg/day orally, and the drug is sold under the trade name Evista™ by Eli Lily. Raloxifene is a selective estrogen receptor modulator (SERM) that in experimental animals acts as an estrogen receptor antagonist in breast and endometrium but as an estrogen receptor agonist in the skeletal and cardiovascular systems. Lufkin et al in Journal of Bone and Mineral Research, 1998:13:1747-1754 entitled: "Treatment of Established Postmenopausal Osteoporosis with Raloxifene: A Randomized Trial", incorporated herein by reference, demonstrated among the raloxifene treated groups and control there were no differences among groups in the occurrence of uterine bleeding, thrombophlebitis, breast abnormalities, or increased endometrial thickness as assessed by ultrasonography. Lufkin et al concluded that that raloxifene therapy for osteoporosis is well tolerated, reduces serum lipids, and does not stimulate the uterus or breasts. Additionally, it was concluded that raloxifene has beneficial effects for reduction of bone mass although the beneficial effects were reported to be of a smaller magnitude than have been reported with estrogen therapy.

Preswood et al compared the effect of estrogen with raloxifene in the Journal of Clinical Endocrinology & Metabolism Vol. 85, No. 6, 2197-2202, entitled: "A comparison of the effects of raloxifene and estrogen on bone in postmenopausal women", incorporated herein by reference. According to Preswood, raloxifene did not decrease activation frequency, bone formation rate or bone volume as did estrogen. Beside being known to have no stimulatory effects on breast and uterus, Snyder et al showed raloxifene may also reduce the incidence of breast cancer and has a positive effect on serum lipids in American Journal of Health-System Pharmacy, Vol. 57, Issue 18, 1669-1675, entitled: "Raloxifene hydrochloride", incorporated herein by reference.

Raloxifene also appears to be superior to other agents such as alendonate that work through the mechanism of inhibiting bone resorbing cells, the osteoclast. Sambrook et al disclosed in Journal of Internal Medicine. 255(4):503-511, entitled: "Alendonate produces greater effects than raloxifene on bone density and bone turnover in postmenopausal women with low bone density: results of EFFECT (Efficacy of FOSAMAX® versus EVISTA® Comparison Trial) International 1", incorporated herein by reference, that alendonate results in high bone density and lower bone turnover comparing to raloxifene. The result of decreased reabsorbtion is increased bone mass although such bone mass may not be normally organized due to the decrease in bone resorption.

Raloxiphene is believed to be useful for potentiating endogenous BMP-2. U.S. Patent Application No. 2005/0271637 to Bodine et al. (the Bodine application) entitled "BMP-2 estrogen responsive element and methods of using the same" incorporated herein by reference, points out that the potentiating effects of estrogen are primarily on the α-estrogen receptor, where the potentiating effect of raloxifene also is believed to occur. Although tamoxiphene has a similar but smaller effect, it also has general systemic effects such as on breast and uterus. The desirable selectivity of raloxifene makes it a medication with improved specificity. The Bodine application showed direct measurable effect of estrogen on endogenous BMP-2 secretion, presumably through its direct effect on related mRNA. The effect of raloxifene is shown to be similar.

It has been found that SERMs are also effective for facilitating bone fusion through its effect on natural bone and connective tissue processes, and based on these results, SERMs can be effective to facilitating the healing of connective tissue generally. Furthermore, it has been found that SERMs have a synergistic efficacy in combination with exogenous BMP. In general, SERMs, therefore, can be used for any patient, although the use of SERMs with postmenopausal women can be particularly desirous since deficiencies of natural hormones for bone healing complicate these processes in this group. SERMs can be administered systemically or through local administration near the desired location for connective tissue healing. Raloxifene can be a desirable SERM for connective tissue healing due to its believed low levels of certain undesirable side effects.

Therefore, raloxifene can be used together with exogenous BMP-2, such as Infuse™ from Medtronic. Raloxifene can be useful for potentiating exogenously applied BMP-2, such as Infuse™ from Medtronic, for connective tissue healing, bone fusion or normal fracture situations, where increased bone turnover is believed to be important. Other members, or their derivatives, or their analogs, in the family of SERM may also be used to facilitate bone healing or other connective tissue healing processes.

In some embodiments, the bone healing process is facilitated by the use of selective estrogen receptor modulator (SERM) such as raloxifene in combination with exogenous BMP-2. Nutritional supplements, such as vitamin D and calcium, endocrine factors, growth factors, and synthetic or natural anabolic steroids can be used in conjunction with SERMs, such as raloxifene, and optional also with BMP, such as BMP-2. Many patients involved in bone related surgical procedures may be nutritionally deficient. The most obvious and common deficiency is vitamin D. Other common micronutrients like silicon or zinc may also play a role. Vitamin D in particular can be used in conjunction with calcium to facilitate the bone healing processes.

Sacroiliac Joint Fusion, Vertebrae Fusion, Bone Repair, Bone Healing and BMP

It has been discovered that bone fusion can be facilitated through the administration of SERMs, in particular raloxifene. The healing response involved in the fusing of joints involves many physiological similarities with other bone healing responses. Bone healing or growth is believed to be influence by cell differentiation and vascularization as well as reorganization of the bone tissue. Beyond simple cell division and differentiation, vascularization and organization of the bone tissue are essential to achieve healed bone. In bone graft and joint fusion surgeries, for example, after surgery at least part of the bone graft or implant remains avascular and unorganized in many patients. Stimulatory agents to facilitate the incorporation of bone implants have been used to help facilitate the bone healing processes. U.S. Patent Application No. 2009/0024174 to Stark et al, entitled: "Bone screws and particular applications to sacroiliac joint fusion", incorporated herein by reference, for example disclosed the use of bone morphogenetic protein (BMP) during sacroiliac joint fusion surgery to facilitate recovery.

Joint fusion can comprise the insertion of an immobilization element into the joint. Suitable immobilization elements can include, for example, shims, wedges, nails, screws, cages, and the like. Any reasonable element can be used. In some embodiments, the immobilization element may be hollow and may be fenestrated to allow bone growth through the wall of the element and into the element. For these embodiments, a therapeutic composition can be placed into the hollow interior of the element for local delivery of the therapeutic composition. Generally, the immobilization element can be constructed from any suitable biocompatible material, such as metals, polymers, ceramic or bone material, or combinations thereof. Suitable metals include, for example stainless steel and/or titanium. Suitable ceramics or bone material include, for example, hydroxyapatite and/or powdered bone. Immobilization elements, such as for sacroiliac joint fusion, are described further in U.S. Pat. No. 7,648,509 to Stark, entitled "Sacroiliac Joint Immobilization," incorporated herein by reference.

Bone morphogenetic proteins (BMPs) are a group of growth factors and cytokines known for their ability to induce the formation of bone and cartilage. Originally, seven such proteins were discovered, of which six including BMP-2 through BMP-7 belong to the transforming growth factor beta (TGF-β) superfamily of proteins. BMP-1 is a metalloprotease. Thirteen more BMPs have since been discovered, bringing the total of known BMPs to twenty. BMPs can now be produced using recombinant DNA technology and have found applications in many disciplines of medicine and dentistry. Orthopedic surgery and oral surgery in particular have benefited greatly from commercially available BMP formulations. A formulation containing natural BMPs for example is available in oral form under the commercial name Ostinol™. It is being marketed as a supplement for bone and joint health by alternative health care practitioners. In regenerative medicine, BMPs are delivered to the site of the fracture, being incorporated into the bone implant, which is then released gradually to facilitate bone formation. The stimulus supplied by BMPs however, can be localized, and it may be useful to sustain the effects for some weeks to achieve measurable improvement. Currently, two BMP products have been approved by the Food and Drug Administration (FDA) for clinical applications including fractures of long bones and intervertebral disk regeneration. The two products are Infuse™ BMP-2 (Medtronic) and OP-1 BMP-7 (Stryker Biotech) where the exogenous BMPs are delivered in a purified collagen matrix, which is then implanted in the site of the fracture. BMP-2 has also been used for spinal fusion procedures and sacroiliac joint fusion procedures. The results of sacroiliac joint fusion procedures with BMP are summarized in the example below.

Referring to FIG. 1, a simplified scheme of bone healing with or without exogenous stimulation agent is shown. First, stem cells differentiate into osteoblasts, which secrete endogenous bone morphogenetic protein 2 (BMP-2). BMP-2 in turn induces osteoblasts differentiation into osteocytes, causes angiogenesis, and stimulates other processes necessary for bone healing. Martine et al. disclosed in Endocrinology Vol. 143, No. 4 1545-1553, entitled "Growth factors-cytokines-oncogenes" incorporated herein by reference, that BMP stimulates angiogenesis through the production of vascular endothelial growth factor (VEGF) by osteoblasts and the VEGF thus produced however is not involved in osteoblasts differentiation. In addition to VEGF, other bone anabolic agent may also be involved in the bone formation process. Kawaguchi et al disclosed in the Journal of Clinical Endocrinology & Metabolism Vol. 86, No. 2 875-880 entitled: "Acceleration of fracture healing in nonhuman primates by fibroblast growth factor-2" incorporated herein by reference, that fibroblast growth factor-2 (FGF-2) accelerates fracture healing and prevents nonunion in primates, and therefore is a likely potent bone anabolic agent for clinical use.

Given the important stimulatory role of the endogenous BMP-2, exogenous BMP-2 is used in surgical procedures to help facilitate bone healing. In general, the exogenous BMP-2 can be administered systemically for example in oral form or locally. The FDA approved BMP products are sold in a form for local delivery. In general, an appropriate BMP can be selected to facilitate bone fusion, bone healing and the healing of other connective tissue, such as cartilage. As used herein, BMP refers to natural purified proteins, synthetic proteins, and effective derivatives thereof as well as nucleic acid coding for the BMP with effective control elements that provide for in vivo expression. BMP is described further in published U.S. patent application 2009/0202638A to Hidaka et al., entitled "BMP Gene and Fusion Protein," incorporated herein by reference. As indicated in the examples below, exogenous BMP-2 may not be sufficient enough to achieve a desired level of bone fusion in some patients. Administration of raloxifene (or a similar selective estrogen receptor modulator) has been demonstrated to improve bone fusion results in patients as discussed in the examples below.

Selective Estrogen Receptor Modulator (SERM) in Tissue Healing

Similar to bone, other connective tissues including, for example, skin, vascular tissues, ligaments, cartilage and tendon also contain receptors that respond to estrogen as well as various exogenous regulatory factors that are agonist or antagonist with respect to estrogen receptors. The methods disclosed herein to facilitate bone healing therefore can be similarly applied to facilitate the connective tissue related healing in general as a result of interactions with similar receptors. Whether or not local or systemic delivery of the SERM is appropriate may be influenced by the particular condition being addressed.

For example, Irie et al. in "Effect of Selective Estrogen Receptor Modulator/Raloxifene Analogue on Proliferation and Collagen Metabolism of Tendon Fibroblast," 56$^{th}$ Annual Meeting of the Orthopaedic Research Society, Poster No. 1117, has shown regulatory effect of estrogen and raloxifene analogue on collagen synthesis and degradation in connective tissue besides bone. Kato et al., in "Raloxifene inhibits TNF-α induced apoptosis via INK-BAD signaling pathway in osteoblastic cells," 56$^{th}$ Annual Meeting of the Orthopaedic Research Society, Poster No. 525, has shown raloxifene has anti-apoptotic effect to protect osteoblastic cells. Hettrich et al. in "The Effect of Recombinant Human Parathyroid Hormone (rhPTI-1) on the Healing of Tendon to Bone in a Rat Model," 56$^{th}$ Annual Meeting of the Orthopaedic Research Society, Poster No. 1105, reported rhPTH improved tendon repair and tendon qualities. All four references are incorporated herein by reference. The method of using SERMs to facilitate tissue healing may be used in patient having connective tissue injury including laceration, contusion, ischemia, anoxia, or avulsion of the connective tissue. Some of the patients who have congenital, endocrine, or nutritional imbalance related to connective tissue may especially benefit from treatments using SERMs. For these applications, the combination with a BMP may also be effective in a synergistic fashion.

Administration of the SERM and Optional BMP or Other Therapeutic Agent

The therapeutic agents discussed herein may be delivered systemically, e.g., via oral route, locally via direct administration into the site of surgery or a combination thereof. Auxiliary delivery agent such as hydrogel for controlled released maybe used to help achieve desired administration effect. The SERM may be administered systemically, topically (for example as a patch), intravenously, intramuscularly, orally, rectally, or locally within the patient such as at the site of a procedure. For example, the SERM can be administered directly to the joint or surrounding tissue to access the immobilization element to facilitate joint immobilization or fusion.

The SERM may be administered from an internal or an external reservoir. In some embodiments, the SERM containing composition may be pre-applied to an immobilization element or a reservoir for administration within the patient.

A BMP can be delivered in conjunction with the SERM, and the BMP may or may not be delivered in an analogous fashion as the SERM. In general, the BMP may be delivered locally or systemically. Desirable results have been obtained with local delivery of BMP for joint fusion, and side effects associated with local delivery have not been generally deleterious on the patients. As noted above, BMP-2 and BMP-7 are available commercially for local delivery into a patient. The commercial BMP-2 is a version derived from recombinant nucleic acid techniques. In alternative or additional embodiments, a BMP can be administered systemically based on an appropriate formulation. Other supplemental agents described above can be administered along with or independently from a SERM, a BMP or a combination thereof for local delivery or systemic delivery.

In summary, a therapeutic composition of relevance herein can comprise a SERM, an optional BMP, an optional supplemental therapeutic agent or a combination thereof. In general, a therapeutic composition can comprise a SERM, and the same composition or additional compositions can comprise an optional BMP and/or an optional supplemental therapeutic agent. Each therapeutic composition can be independently formulated as either an agent for localized delivery or for systemic delivery, and for time-dependent delivery by certain preferred timings and routes. Significant versatility can be obtained through the selective delivery of the agents, although other conveniences can be achieved through simultaneous delivery.

Systemic doses of a therapeutic agent generally can be repeated for a period of time. For example, doses can be administered multiple times in a day, once a day or less frequently. The frequency may depend on the rate of metabolism or otherwise removal from the patient's body. The total treatment period can be select to account for the healing or fusing process. For example, the treatment can be continued in some embodiments for a period of three months, for a period of one month, intermediate period, longer periods or shorter periods as appropriate. Local delivery of a therapeutic agent generally is performed once, although in principle local delivery of a therapeutic agent near the site of connective tissue healing can be repeated. The local delivery of the therapeutic agent can involve a vehicle that provides for gradual or timed release of the therapeutic agent to keep the local dose of the therapeutic agent near desired values.

For local delivery, the dosage amount of a SERM composition administered to a patient may be determined by physical and physiological factors such as body weight, severity of condition, previous or concurrent therapeutic interventions, individualized for the patient and by the route of administration. The practitioner responsible for administration can, in any event, determine the concentration of active ingredient(s) in a composition and appropriate dose(s) for the individual subject.

In certain embodiments, pharmaceutically acceptable compositions may comprise, for example, at least about 0.1% of a SERM compound. In other embodiments, the active compound may comprise between about 2% to about 75% of the weight of the unit, or between about 25% to about 60%, for example, and any range derivable therein. In other non-limiting examples for local delivery, a local dose may also comprise the equivalent of at least about 1 microgram/kg-body weight, about 5 microgram/kg-body weight to about 1000 mg/kg-body weight, about 25 microgram/kg/body weight to about 750 mg/kg-body weight, about 100 microgram/kg-body weight to about 500 mg/kg-body weight, about 500 microgram/kg-body weight to about 250 mg/kg-body weight, and in further embodiments about 1 milligram/kg-body weight to about 100 milligram/kg-body weight. For systemic delivery in some embodiments, daily doses can be in the range of about 1.0 mg/kg-body weight to about 500 mg/kg-body weight, in further embodiments from about 2.0 mg/kg-body weight to about 300 mg/kg-body weight and in other embodiment from about 5 mg/kg-body weight to about 250 mg/kg-body weight. Systemic doses can be continued for an effective period of time during the healing process, such as from about 1 day to about 12 months, or longer depending on the goal and patient response. In some cases the SERM may be continued for years. In further embodiments from about 4 days to about 9 months, and in additional embodiments from about 7 days to about 6 months. A person of ordinary skill in the art will recognize that additional ranges within the explicit ranges above are contemplated and are within the present disclosure.

The administration of the SERM may occur before, after or simultaneously with the BMP agent and may be to a single targeted site or separate sites. Local delivery of the therapeutic composition of BMP or SERM and other pharmacologic or endocrine components involves delivery of a quantity of the therapeutic composition in the vicinity of the bone or other connective tissue that is targeted for healing, fusion or the like. The therapeutic agent associated with the therapeutic composition can be delivered over time. While some of the therapeutic agent can migrate from the treatment site, the local delivery can involve an overall reduced dose such that potential side effects are correspondingly reduced. Thus, SERMs can be delivered to individuals to facilitate connective tissue healing with reduced risks of undesired effects.

Local delivery can be effectuated with an appropriate tool to provide for the delivery. For example, the therapeutic composition can be placed into an immobilization element or coated onto an immobilization element. Alternatively or additionally, the therapeutic composition can be separately placed at the site of the procedure using, for example, a syringe, a spatula, forceps or other suitable tool. The selection of the tool can be based on the nature of the therapeutic composition. In general, the therapeutic composition can be, for example, a viscous liquid, e.g., a suspension, a powder, a gel, a solid or other suitable form or combination of forms. In general, the therapeutic composition is selected so that it does not migrate far from the site where the composition is placed. In some embodiments, the therapeutic agent can be gradually released. For example, the therapeutic agent can be associated with a resorbable medium, such as a collagen material, a bone material, a biodegradable polymer, suture, combinations thereof or the like.

The dose of BMP may be highly selective, based on methods of administration and the particular procedure on the patient. Endogenous BMP is produced by many cells in the maturing connective tissue situation, including osteoblasts, mesenchymal cells and chondrocytes. In an untreated natural situation of healing, BMP can be delivered to be concentrated in the area, or be continually released, to have its local effects dominate. In a normal untreated fracture, the amount of endogenous BMP is very low. Typical dosages used with the Medtronic Infuse™ system, administered on a collagen sponge depot, for example can range from approximately one milligram rhBMP-2 for a cervical fusion to 12 mg or more for complex or large spinal fusions. The dose appropriate with cotreatment with a SERM, endocrine, or nutritional factors may be more or less, depending on type of BMP used, timing of release, local physiology, age of patient, and the specific combination of growth, stimulation or nutritional factors. In some embodiments, BMP doses can be in the range of about 0.1 mg to about 60 mg, in further embodiments from about 0.5 mg to about 30 mg and in other embodiment from about 1.2 mg to about 10 mg. The time release composition can comprise an appropriate concentration, and the commercial product is believed to comprise about 1.5 mg/mL concentration in a liquid that is absorbed into a collagen matrix. A person of ordinary skill in the art will recognize that additional ranges within the explicit ranges above are contemplated and are within the present disclosure. The BMP generally is gradually released.

For local delivery, a therapeutic composition comprising a SERM or other therapeutic agent may be formulated in a polymer coating that affords controlled release through the healing period following bone or tissue related trauma or surgery. In some embodiments SERM may be encapsulated in polymeric nanoparticles for sustained control release. Alternatively, hydrogel such as collagen can be used. For example, commercially available BMP such as Infuse™ is dissolved in water which is then soaked up in a collagen sponge for controlled release and sustained delivery. An examplatory osteogenic collagen sponge composition is disclosed in U.S. Pat. No. 7,563,455 to McKay et al., entitled "Highly-mineralized osteogenic sponge compositions, and uses thereof", incorporated herein by reference. Polymeric nanoparticles encapsulated SERM can be suspended in water or biocompatible buffer to be soaked up together with BMP into the collagen sponge for controlled and sustained delivery.

The SERM compounds may be provided as pharmaceutically acceptable salts, or in pharmaceutically acceptable diluents or excipients. Pharmaceutically acceptable salts of the compounds described herein may be synthesized according to methods known to those skilled in this art, see, for example Pharmaceutical Salts: Properties, Selection, and Use, P. Heinrich Stahl (Editor), Camille G. Wermuth (Editor) June 2002. Generally, such salts are prepared by reactions of the free base forms of these compounds with a stoichiometric amount of the appropriate acid in water or in an organic solvent, or in a mixture of the two; generally, nonaqueous media like ether, ethyl acetate, ethanol, isopropanol, or acetonitrile generally are suitable. Lists of some appropriate salts are found, for example, in Remington's Pharmaceutical Sciences, 17th ed., Mack Publishing Company, Easton, Pa., 1985.

For systemic delivery, the therapeutic composition can be formulated, for example, for injection, intravenous delivery, oral delivery, transdermal patches or other suitable delivery technique. Systemic delivery involves the administration of the composition for circulation through the patient's body. In some embodiments, the therapeutic composition, which may comprise a SERM, can be administered orally in solid dosage forms, such as capsules, tablets, and powders, or in liquid dosage forms, such as elixirs, syrups, and suspensions. The SERM can also be administered parenterally, in sterile liquid or in depot administration dosage forms.

The SERM compounds may be administered in oral dosage forms that can include, for example, tablets, capsules, pills, powders, granules, elixirs, tinctures, suspensions, syrups, and emulsions. Oral ingestion forms of some serves are presently commercially available. Further, the compounds may be administered in intravenous (bolus or infusion), intraperitoneal, subcutaneous, or intramuscular form. An effective amount of the SERM compounds described herein can be administered in a mixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. In some embodiments, the deliverable compound can be in a form suitable for oral, rectal, topical, intravenous injection or parenteral administration. Suitable carriers combined with the therapeutic agents can comprise solids or liquids, and the type of carrier can be chosen based on the type of administration being used. The effective amount can be determined as an amount that provides some relief from the symptoms to be alleviated.

Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.).

Suitable binders, lubricants, disintegrating agents, coloring agents, flavoring agents, flow-inducing agents, and melting agents may be included as suitable components for therapeutic compositions, e.g., for pills. For instance, an active drug component, i.e. therapeutic agent(s), can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like for appropriate embodiments.

Suitable binders can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms can include sodium oleate, sodium stearate, magnesium stearate, sodium benzoate, sodium acetate, sodium chloride, and the like. Disintegrators can include, for example, starch, methyl cellulose, agar, bentonite, xanthan gum, and the like.

The compounds may also be coupled to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels. In some embodiment, the composition disclosed herein can be embedded in biodegradable sutures for controlled release to facilitate healing. The suture can be placed at or near a joint for fusion or other connective tissue for appropriate treatment.

Capsules may contain the SERM and/or other therapeutic agent described herein, and powdered carriers, such as lactose, starch, cellulose derivatives, magnesium stearate, stearic acid, and the like. Similarly, such diluents can be used to make compressed tablets. Both tablets and capsules can be manufactured as immediate release products or as sustained release products to provide for continuous or long-term release of the active compounds. The deliverable form of the SERM can be sugar coated or film coated to mask any unpleasant taste and protect the tablet from the atmosphere, or enteric coated for selective disintegration in the gastrointestinal tract.

For oral administration as a liquid, the drug components may be combined with any oral, non-toxic, pharmaceutically acceptable inert carrier such as ethanol, glycerol, water, and the like. Example liquid forms include, for example, solutions or suspensions in water, pharmaceutically acceptable fats and oils, edible alcohols or other non-toxic organic solvents, including esters, emulsions, syrups or elixirs, suspensions, solutions and/or suspensions reconstituted from non-effervescent granules and effervescent preparations reconstituted from effervescent granules. Liquid dosage forms may contain, for example, suitable solvents, preservatives, emulsifying agents, suspending agents, diluents, sweeteners, thickeners, and melting agents.

Liquid dosage forms for oral administration can contain coloring and flavoring, as needed. In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The SERM described herein may also be administered in intranasal form via use of suitable intranasal vehicles, or via transdermal routes, using those forms of transdermal skin patches known to those skilled in these arts. To be administered in the form of a transdermal delivery system, the dosage administration can be effectively continuous for at least stretches of time rather than intermittent throughout the dosage regimen. Parenteral and intravenous forms may also include minerals and other materials to make them compatible with the type of injection or delivery system chosen.

The SERM and/or other therapeutic agent set forth herein may also be used in pharmaceutical kits which comprise one or more containers containing a pharmaceutical composition comprising a therapeutically effective amount of the SERM. An effective amount can be determined as an amount that provides some relief from the symptoms to be alleviated. Such kits may further include, if desired, one or more of various components, such as, for example, containers with the compound, containers with one or more pharmaceutically acceptable carriers, additional containers, and instructions. The instructions may be in printed or electronic form provided, for example, as inserts or labels, indicating quantities of the components to be administered, guidelines for administration, and/or guidelines for mixing the components.

EXAMPLES

Example 1

Results from Surgeries Performed with and without Exogenous BMP

This example is directed to demonstrate the efficacy of BMP-2 to stimulate bone fusion in sacroiliac joint procedures.

A series of sacroiliac joint fusion surgeries were performed using an open procedure to expose the sacroiliac joint. Exogenous BMP treatment was introduced at the site of surgery to some patients. The union and non-union rate of the sacroiliac joint 3 month intervals after the surgeries were compared. Significant improvement in union rate is shown in surgical cases where exogenous BMP was delivered locally at the site of the fusion. Specifically, BMP-2 (Infuse™ from Medtronic) was placed into the site in association with a collagen sponge along with a spinal fusion cage and bone graft. The union and non-union frequencies of sacroiliac joint fusion surgeries performed using the open procedure with and without exogenous BMP are analyzed and the results are listed in Table 1. Although there are variations in the techniques used in the cases, and most of the with-BMP cases came later in the series, a chi-square test of the results has a $p<0.00001$, indicating statistically significant difference in the rate of fusion between the with and without BMP groups.

TABLE 1

| Sacroiliac Fusion Cases | | |
|---|---|---|
| | Union | Non-Union |
| with-BMP | 70 | 1 |
| without BMP | 45 | 18 |

Figure 2:
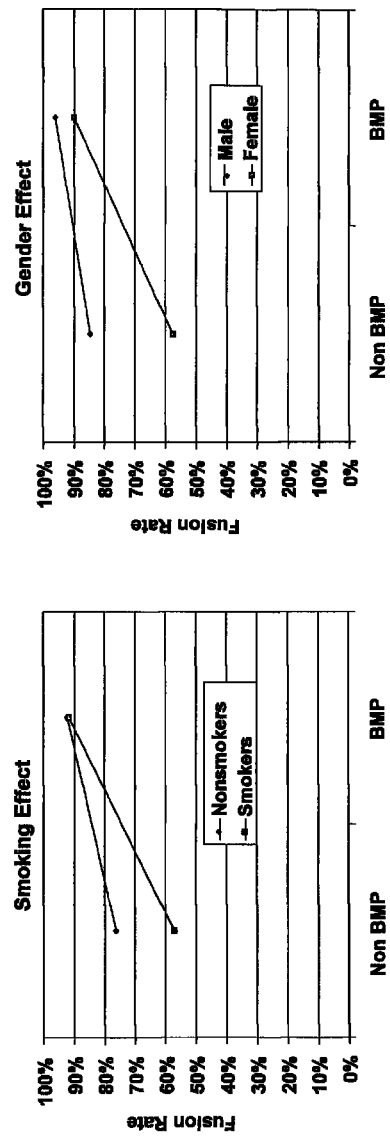
FIG. 2 is a histogram plot of the sacroiliac joint fusion rate of (a) patients who are smokers or non-smokers and (b) male or female patients, with or without post-surgery exogenous BMP.

The influence of BMP on the outcome of the surgeries was further analyzed in different patient sub-groups. As shown in FIG. 2 (a), while non-smokers responded favorably for the use of BMP, the effect is more pronounced for smokers. In fact, the use of BMP has filled the fusion rate gap between the smokers and non-smokers. When BMP was not used, the fusion rate of smokers is significantly (about 20%) lower than the non-smokers, which is expected given the known adverse effect of tobacco smoking on bone healing. When BMP is used, however, both the smoker and non-smoker appear to have fusion rate of >90%. FIG. 2 (b) shows the effect of BMP usage on female and male patients. When BMP was not used, the fusion rate of male patients is significantly (about 25%) higher than the female patients. When BMP is used, the gap between the fusion rate of male and female patient shrank to less than 10% and both patient group appear to have fusion rate of 90% or greater.

Example 2

Bone Morphogenetic Protein Alone for Bone Fusion

This example is directed to results of sacroiliac joint fusion in post menopausal women using exogenous BMP-2 administered at the joint.

Figure 3:
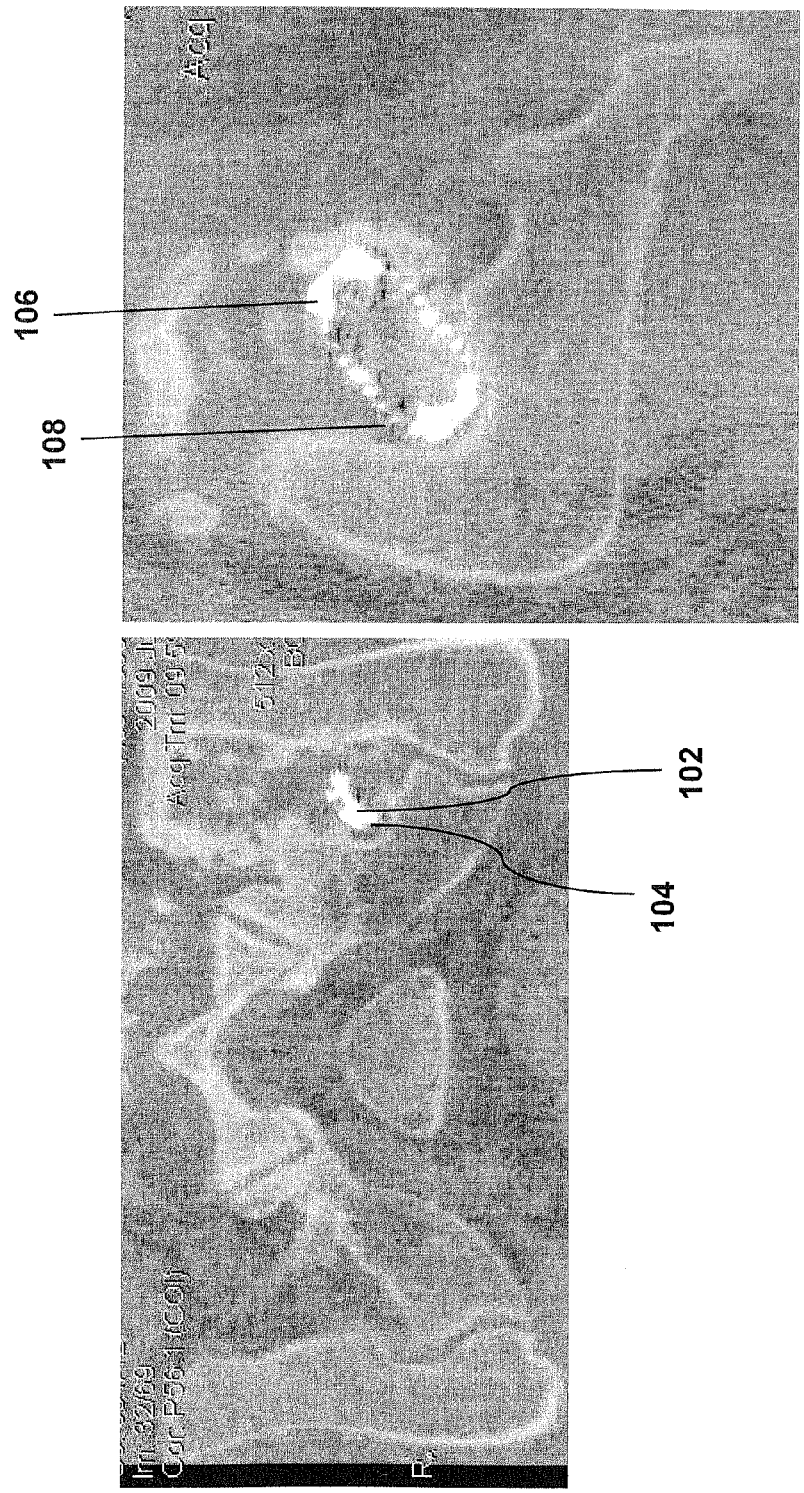
FIG. 3 is a set of photographs taken from sacroiliac joint fusion or immobilization in postmenopausal females showing compromised incorporation.

Joint fusion surgeries were performed either using an open procedure exposing the joint, as described in Example 1, or using a less invasive procedure similar to the procedures described in U.S. Patent Application No. 2009/0024174 to Stark et al, entitled: "Bone screws and particular applications to sacroiliac joint fusion", incorporated herein by reference. With either procedure, a spinal fusion cage was inserted to fuse the joint, and BMP-2 (Infuse™) was placed in the joint with a collagen sponge. The results with the open and closed procedure were comparable. Some of the patients involved in this study were female at age of over 60 years old. Exogenous BMP-2 was dosed at the time of surgery around the graft. The bone healing was examined by computerized tomography three months after surgery and the results are shown in FIG. 3, where the compromised incorporation of bone grafts in postmenopausal females are visible. In FIG. 3(a), there exist a significant gap 104 between the bone graft 102 and the host bone. In FIG. 3(b), a significant gap 108 is shown to be between the bone graft 106 and the host bone. The localized administration of bone morphogenetic protein to facilitate joint fusion/immobilization therefore appears to be insufficient for some patients, especially postmenopausal women.

Figure 4:
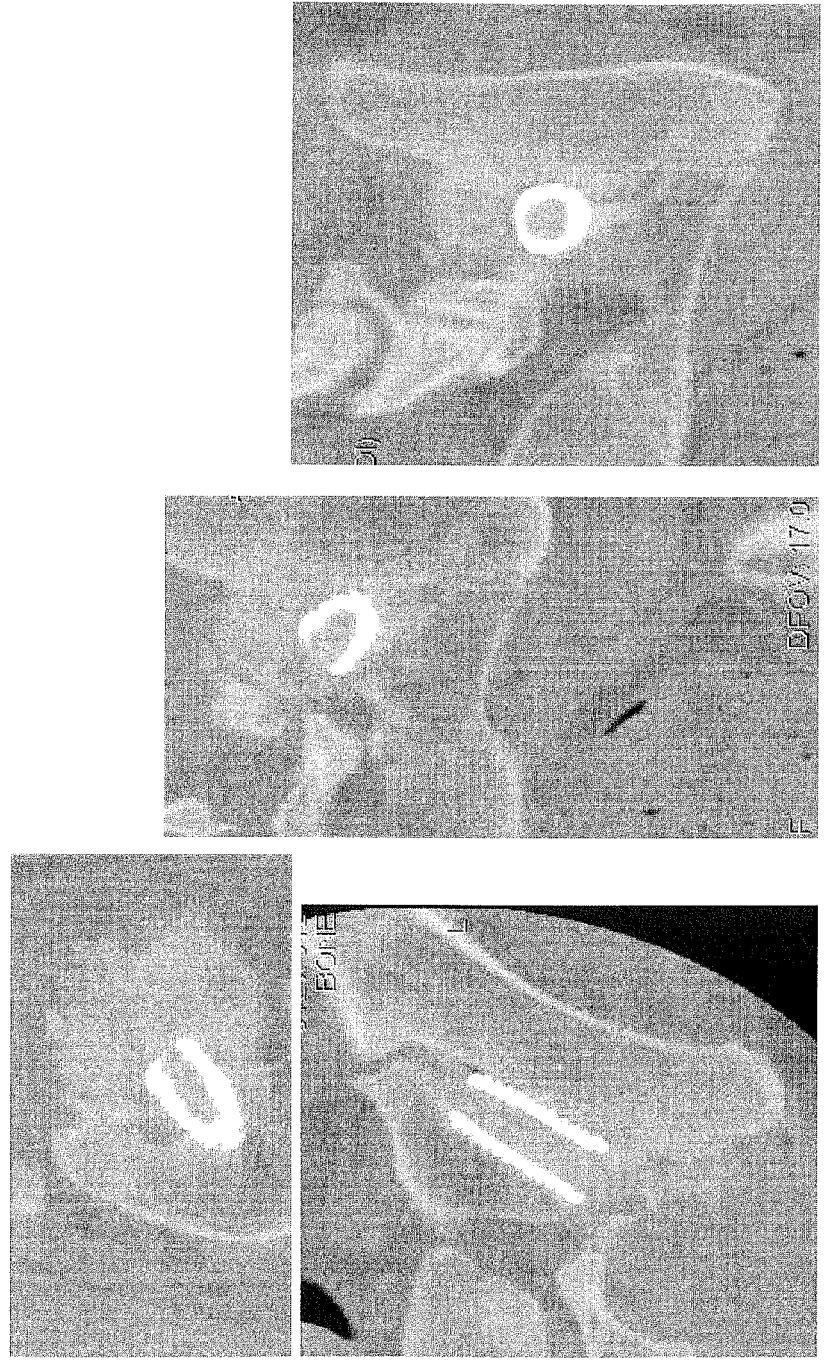
FIG. 4 is a set of photographs taken from different perspectives of a sacroiliac joint fusion or immobilization in a 30 year old male. The results obtained for this patient with the absence of raloxifene exhibit less advanced incorporation as compared to the postmenopausal female of FIG. 5.

FIG. 4 shows various perspective computerized tomography images of host bone with graft of a healthy 30 year old male, three months after the surgery. The male patient, although having a normal healthy recovery, the bone graft does not show similar maturity and healing of the 60+ year old postmenopausal woman who received both local BMP-2 and oral raloxifene, as discussed in Example 3 below. Raloxifene thus seems to have potentiated healing processes that is better than normal healing.

Example 3

The Effect of Raloxifene on Bone Healing

This example demonstrates the effectiveness of raloxifene to improve the effectiveness of sacroiliac joint fusion in postmenopausal women.

Joint fusion surgeries were performed using a less invasive procedure similar to the procedures described in U.S. Patent Application No. 2009/0024174 to Stark et al, entitled: "Bone screws and particular applications to sacroiliac joint fusion", incorporated herein by reference. The patients involved in the study were female at age of over 60 years old. Raloxifene (60 mg/day) was administered orally to some female patients after bone fusion surgery for three months. During the bone fusion surgery, a spinal cage was inserted to fuse the joint and BMP-2 associated with a collagen sponge (Infuse™) was placed into the site during the procedure. Exogenous BMP-2 was dosed at the time of surgery around the graft both in control and in raloxifene treated patients. Significant improvement in bone healing is observed in raloxifene treated patients. Referring to FIG. 3, computerized tomography images of the host bone in a raloxifene treated patient from two perspectives are shown. The three month old graft 112 appears to be fully healed and incorporated into the host bone. The healed bone portion 114 has "ground glass" mature bone appearance, which is difficult to achieve anywhere in the bone healing situations, except with the passage of long periods of time. It is all the more evident within the implant, because the graft is relatively avascular there, where it is isolated by the implant walls.

Figure 5:
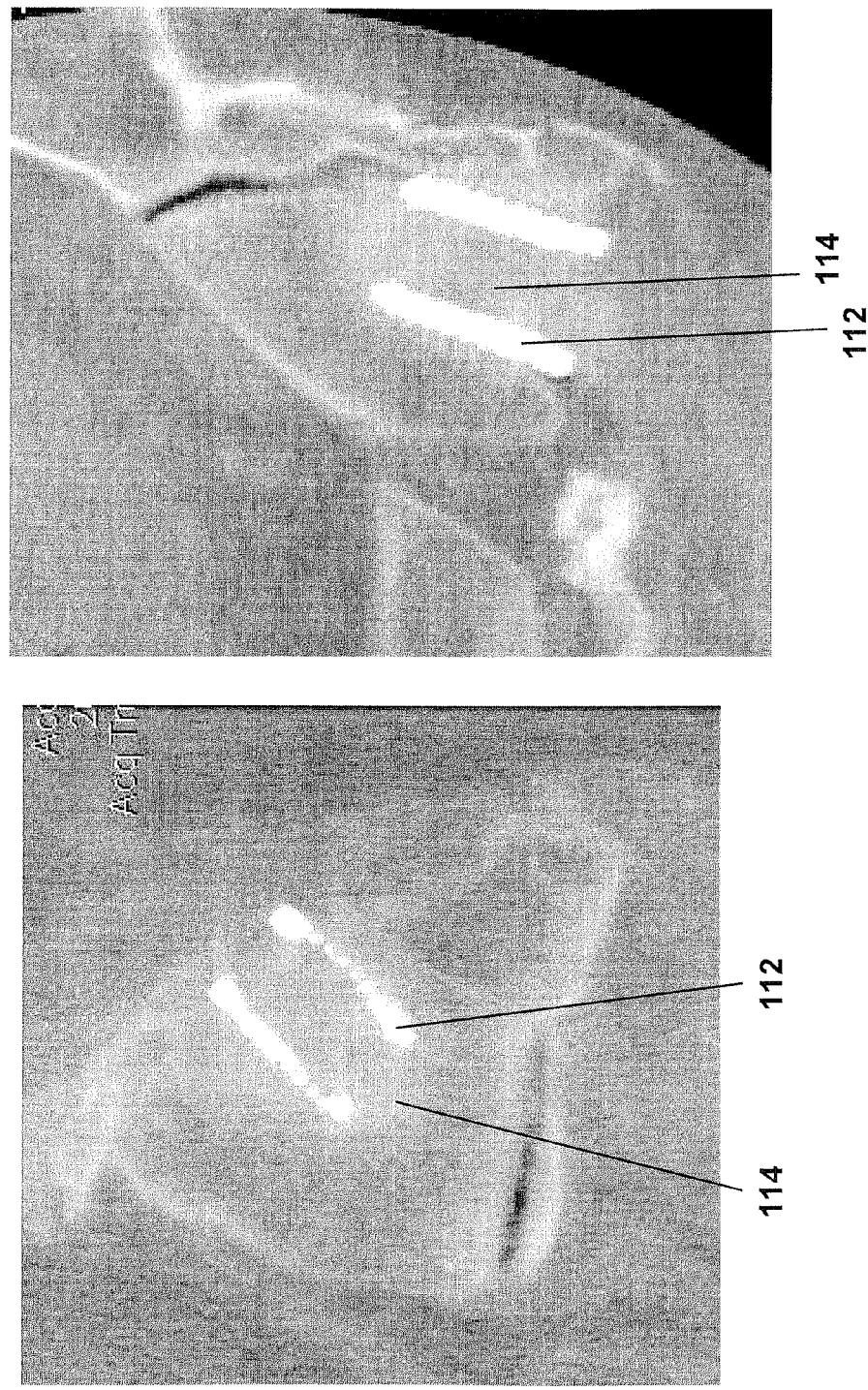
FIG. 5 is a set of photographs taken from different perspectives of a sacroiliac joint fusion or immobilization in a postmenopausal female administered with raloxifene showing improved incorporation.

These results suggest that the accelerated superior healing of the bone graft is the result of oral raloxifene administration. The results indicate that the combination of therapeutic agents (BMP-2 and raloxifene) result in the combined effects of revascularization, stem cell differentiation, cytokine secretion, cell proliferation, and importantly, bone turnover, leading to the mature bone appearance and fully incorporated bone graft shown in FIG. 5.

Figure 6:
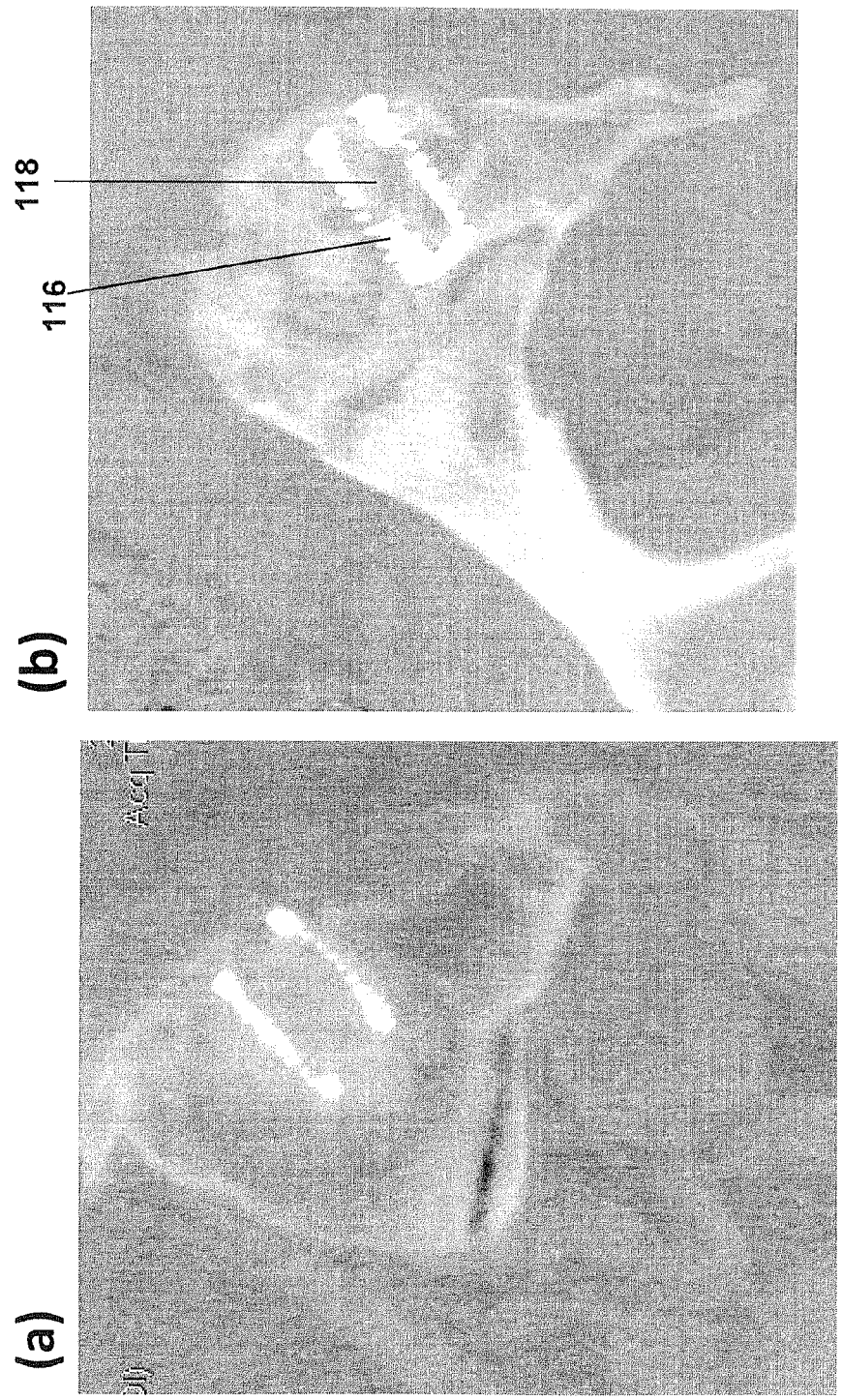
FIG. 6 is a set of photographs providing comparative results from two postmenopausal female patients who had sacroiliac joint fusion or immobilization surgeries showing (a) improved incorporation for the patient who received post surgery raloxifene and (b) compromised incorporation for the patient who did not receive raloxifene.
Figure 7:
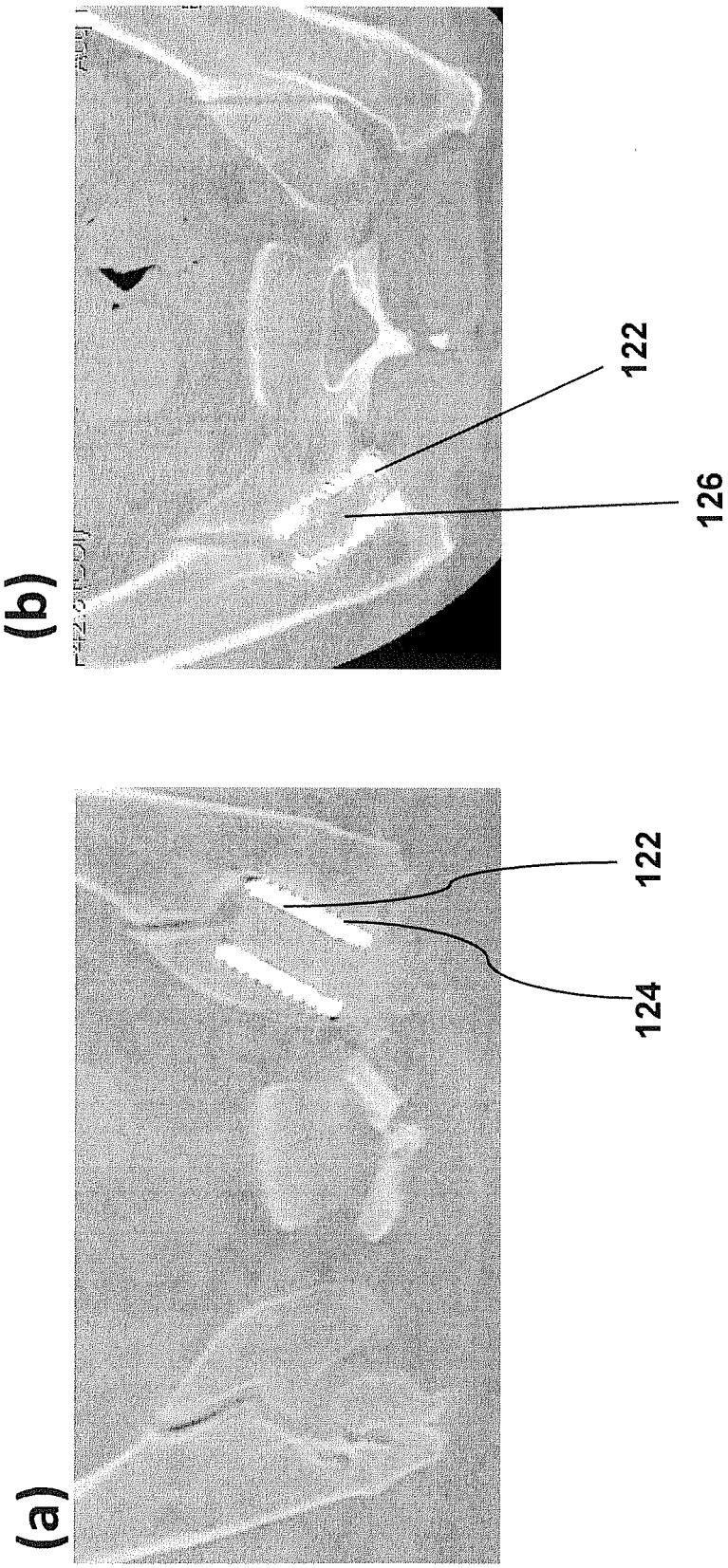
FIG. 7 is another set of photographs taken following sacroiliac joint fusion or immobilization in two postmenopausal females showing (a) improved incorporation for the patient who received post surgery raloxifene and (b) compromised incorporation for the patient who did not receive raloxifene.

The results from the raloxifene treated patients are further compared with patients treated with exogenous BMP-2 only and the results are shown in FIGS. 6 and 7. As shown in FIG. 6, the left image FIG. 6(a) shows X-ray image of the host bone of raloxifene/BMP-2 treated patients having fully incorporated bone graft and with the bone took on an overall mature appearance. The right image FIG. 6(b) is computerized tomography image of the host bone of a patient treated with exogenous BMP-2 only, showing the bone graft 116 not fully incorporated with gaps 118 appear round the bone graft 116. Similarly, for two other patients who had the bone fusion surgery, the patient who was under treatment with raloxifene/BMP-2 shows the incorporated bone graft 122 appears to have incorporated surrounding 124 and took on a mature bone appearance in FIG. 7(a). In contrast, for the patient who received BMP-2 only, though healing to some degree occurred with BMP without raloxifene as shown in FIG. 7(b), the overall bone healing is not as mature as the patients in FIG. 7(a) as evident by the lack of maturity within the implant 122, with problem area 126, where the stress of failed revascularization and failure of growth is probably greatest.

These results suggest a synergistic effect of raloxifene and exogenous BMP-2. The results obtained for postmenopausal women were observed to be better with the combination of raloxifene and BMP-2 than the results obtained from a 30 year old male patient who received BMP-2, as described above in Example 2. Therefore, it would be expected that raloxifene or other suitable SERM would also have beneficial effects for bone fusion if administered to men and to pre-menopausal women.

The bone graft procedures, while done equivalently, because the difference of with or without oral raloxifene administration, can yield significantly different results. Patients with fully incorporated bone graft such as those shown in FIG. 5 and FIG. 6(a) may have no pain after the three month treatment period. In contrast, delayed healing, pain, and future surgery may very likely to be necessary for patients who fail to incorporate the bone graft such as those shown in FIG. 6(b) and FIG. 7.

In some treatment cases, the oral administration of raloxifene is initiated until sometime after the bone fusion surgeries. The bone healing or bone graft incorporation in the delayed raloxifene administration cases are not as complete as when raloxifene was administered immediately following the surgery. When compared with control patients where BMP-2 only is administered, however, some patients with delayed raloxifene administration seemed to show superior recovery results. The improvement effect shown by the delayed raloxifene administration may be advantageous in some situations when raloxifene can not be administered immediately after surgery due to other medical concerns.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. All patents, patent applications, and publications referenced herein are hereby incorporated by reference herein to the extent that the incorporated material is not contrary to any of the explicit disclosure herein.

I claim:

1. A method for the improvement of bone healing, the method comprising: administering locally an effective amount of a composition comprising a selective estrogen receptor modulator (SERM) to a patient, to improve the bone healing process wherein the patient also receives an osteoconductive material.

2. The method of claim 1 wherein the osteoconductive material comprises bone powder, bone segments, hydroxyapatite, tricalcium phosphate, other synthetic bone-like materials, or combinations thereof.

3. The method of claim 1 wherein the bone healing process comprises administering the effective amount of composition to a patient that has received an immobilization element interfacing with a joint, to result in joint immobilization or fusion.

4. The method of claim 1 further comprising administering a bone morphogenetic protein (BMP) to the patient to facilitate bone healing.

5. The method of claim 4 wherein the BMP is BMP-2, BMP-7, or a combination thereof.

6. The method of claim 1 further comprising administering a cellular cytokine to the patient to facilitate bone healing.

7. The method of claim 1 wherein the SERM is afimoxifene, arzoxifene, bazedoxifene, clomifene, femarelle, lasofoxifene, ormeloxifene, tamoxifen, toremifene, analogs or derivatives thereof, or a combination thereof.

8. The method of claim 1 wherein the SERM is raloxifene, analogs or derivatives thereof, or a combination thereof.

9. The method of claim 1 further comprising administering systemically calcium, vitamin D, or a combination thereof in addition to the SERM to improve bone healing.

10. The method of claim 1 further comprising administering nutritional factors, endocrine factors, growth factors, synthetic or natural anabolic steroids, or a combination thereof in addition to the SERM to improve bone healing.

11. The method of claim 1 wherein the SERM is administered directly to location selected for bone healing.

12. The method of claim 1 wherein the SERM is administered to the tissue surrounding the location of bone healing.

13. The method of claim 1 wherein the bone healing process comprises fusion of adjacent vertebrae.

14. The method of claim 1 wherein the bone healing process comprises fusion of the sacroiliac joint.

15. The method of claim 1 wherein the patient is a postmenopausal woman.

16. A method for the improvement of bone healing, the method comprising: administering locally an effective amount of a composition comprising a selective estrogen receptor modulator (SERM) to a patient, to improve the bone healing process-wherein the composition is controllably released from a suture.

17. A method for the improvement of bone healing, the method comprising: administering BMP locally to the bone location for healing and administering an effective amount of a composition comprising a selective estrogen receptor modulator (SERM) to a patient, to improve the bone healing process wherein the patient is a post-menopausal woman.

18. The method of claim 17 wherein the SERM is administered directly to the bone healing location or surrounding tissue.

19. The method of claim 17 wherein the SERM is administered systemically.

20. The method of claim 17 wherein the SERM is raloxifene, analogs or derivatives thereof, or a combination thereof.

21. The method of claim 17 wherein the BMP is BMP-2, BMP-7, or a combination thereof.

22. The method of claim 17 wherein the bone healing comprises fracture union by traumatically induced fracture mechanisms, stress fractures, or un-united fractures.

23. The method of claim 17 wherein the fusion or immobilization involves fusion of the sacroiliac joint.

24. The method of claim 3 wherein the composition is placed into the interior of the immobilization element.

25. The method of claim 3 wherein the composition is formulated for controlled release of the SERM.

* * * * *